US00RE43371E

(19) United States
(12) Reissued Patent
Scalfaro et al.

(10) Patent Number: US RE43,371 E
(45) Date of Reissued Patent: May 8, 2012

(54) USE OF SELECTED CYCLOSPORINS FOR THE TREATMENT OF HEPATITIS C INFECTION

(76) Inventors: Pietro Scalfaro, Cully (CH); Jean-Maurice Dumont, Vaud (CH); Gregoire Vuagniaux, Vaud (CH); Rolland-Yves Mauvernay, Fribourg (CH)

(21) Appl. No.: 12/915,370

(22) Filed: Oct. 29, 2010

Related U.S. Patent Documents

Reissue of:
(64) Patent No.: 7,439,227
Issued: Oct. 21, 2008
Appl. No.: 11/406,800
Filed: Apr. 12, 2006

U.S. Applications:
(63) Continuation of application No. PCT/IB2005/02940, filed on Oct. 3, 2005.

(30) Foreign Application Priority Data

Oct. 1, 2004 (WO) ..... PCT/IB2004/003205

(51) Int. Cl.
*A61K 38/13* (2006.01)
(52) U.S. Cl. ..... 514/11; 514/4.3; 514/20.5
(58) Field of Classification Search ..... None
See application file for complete search history.

(56) References Cited

U.S. PATENT DOCUMENTS 6,927,208 B1 * 8/2005 Wenger et al. ..... 514/9

FOREIGN PATENT DOCUMENTS

| | | |
|---|---|---|
| WO | WO 98/28328 | 7/1998 |
| WO | WO 98/28329 | 7/1998 |
| WO | WO 00/01715 | 1/2000 |
| WO | WO 2005/021028 | 3/2005 |

OTHER PUBLICATIONS

Watashi et al., Hepatology, 2003, vol. 38, pp. 1282-1288.*
Nakagawa et al., Specific inhibition of hepatitis C virus replication by cyclosporin A. Biochem. Biophys. Res. Commun. 313: 42-7 (2004).
Watashi, K. et al., Cyclosporin A suppresses replication of hepatitis C virus genome in cultured hepatocytes. Hepatology 38: 1282-1288 (2003).
Inoue K. et al., Interferon combined with cyclosporine treatment as an effective countermeasure . . . Transplantation Proceedings, Orlando, FL, vol. 37, pp. 1233-1234, 2005.
Inoue K. et al., Combined interferon alpha2b and cyclosporin A . . . J. Gastroenterol. 38: 567-72 (2003).
Huebler F. et al., Synthetic routes to NEt-Xaa4-cyclosporin A derivatives as potential anti-HIV I drugs. Tetrahedron Lett. (Elsevier, Amsterdam) 41:7193-6 (2000).
Xia Wei-Liang et al., Inhibitory effect of cyclosporine A on hepatitis B . . . Hepatobiliary & Pancreatic Diseases International 4: 18-22 (2005) (ISSN 1499-3872).
Hansson M. et al., The nonimmunosuppressive cyclosporin analogs NIM811 and UNIL025 . . . J. Bioenergetics & Biomembranes (Plenum, N.Y.) 36: 407-13 (2004).

* cited by examiner

*Primary Examiner* — Cecilia Tsang
*Assistant Examiner* — Roy Teller
(74) *Attorney, Agent, or Firm* — McAndrews, Held & Malloy Ltd.

(57) ABSTRACT

This invention relates to the use in the treatment of HCV infection, either as single active agents or in combination with another active agent, of a cyclosporin having increased cyclophilin binding activity and essentially lacking immunosuppressive activity.

1 Claim, 2 Drawing Sheets

USE OF SELECTED CYCLOSPORINS FOR THE TREATMENT OF HEPATITIS C INFECTION

Matter enclosed in heavy brackets [ ] appears in the original patent but forms no part of this reissue specification; matter printed in italics indicates the additions made by reissue.

*The present application is a reissue application of U.S. Pat. No. 7,439,227 which issued Oct. 21, 2008 based on U.S. application Ser. No. 11/406,800 which was filed on Apr. 12, 2006 as a continuation of the International Patent Application No. PCT/IB2005/02940, which was filed Oct. 3, 2005, claiming the benefit of priority of International Patent Application No. PCT/IB2004/003205, which was filed on Oct. 1, 2004.*

TECHNICAL FIELD:

The present invention relates to the use of a cyclosporin for the treatment of hepatitis C virus (HCV) infection and to a pharmaceutical composition comprising said cyclosporin.

BACKGROUND OF THE INVENTION:

HCV was cloned and characterized about 15 years ago by Choo and colleagues (see Science 244, (1989), 359-362). HCV belongs to the family Flaviviridae and comprises an enveloped nucleocapsid and a single-stranded RNA genome of positive polarity (see Bartenschlager et al., Antiviral Res. 60, (2003), 91-102). HCV is transmitted primarily by blood, blood products and vertical transmission during pregnancy. Introduction of diagnostic tests for screening blood products has significantly reduced the rate of new infection.

Still, HCV remains a serious medical problem. There are currently about 170 million people infected with HCV. The initial course of infection is typically mild. However, the immune system is often incapable of clearing the virus, and people with persistent infections are at a high risk for liver cirrhosis and hepatocellular carcinoma (see Poynard et al., Lancet 349, (1997), 825-832).

There is no vaccine available, and therapeutic options are very limited (see Manns et al., Indian J. Gastroenterol. 20 (Suppl. 1), (2001), C47-51; Tan et al., Nat. Rev. Drug Discov. 1, (2002), 867-881).

Current therapy is based on a combination of interferon alpha and ribavirin. This therapy produces a sustained antiviral response in 85-90% of patients infected with genotypes 2 and 3, but, unfortunately, only in about 45% of patients infected with the prevalent genotype 1. Furthermore, side effects are significant and include myalgia, arthralgia, headache, fever, severe depression, leucopenia and haemolytic anaemia.

Clearly, additional therapies, with a higher antiviral activity and a better safety profile, are required for the treatment of HCV infection, particularly e.g. in the case of the prevention of HCV recurrence. In order to establish the safety profile, criteria such as low cytotoxicity and cytostatic and high selectivity index are particularly relevant for clinical treatment of HCV infection.

A novel approach for the treatment of HCV infection using cyclosporins was recently described by clinical observations (see Teraoka et al., Transplant Proc., 1988, 20 (3 suppl 3), 868-876, and Inoue et al. J Gastroenterol, 2003, 38, 567-572).

Recently it was shown that Cyclosporin A (CsA) inhibited the in vitro intracellular replication of an HCV subgenomic replicon at clinically achievable drug concentrations (see Watashi et al., Hepatology 38, 2003, 1282-1288, and Nakagawa et al., BBRC 313, 2004, 42-47). Both groups suggested that the anti-HCV effect of CsA was not associated with immunosuppressive activity based on observations made with the use respectively of an immunosuppressive macrolide, i.e. the compound known under the name FK 506 and a non-immunosuppressive Cyclosporin A derivative, i.e. the compound known under the name NIM 811 or [Melle]$^4$-CsA. Nakagawa et al. consider that expanding applications of CsA may cause substantial problems due to its well-known immunosuppressive properties and suggest that one solution to overcome this problem would be to consider the use of non-immunosuppressive cyclosporin analogs.

During the last 15 years, a number of medicinal chemistry studies have been conducted with the aim to identify such non-immunosuppressive cyclosporin analogs and compound NIM 811 is one of the most representative compounds having such a property.

NIM 811, along with 9 other Cyclosporin A derivatives, were reported by Ko et al. in patent application EP 0 4840 281 for their non-immunosuppressive properties and were considered as being potentially useful in the treatment of HIV infection and the prevention of AIDS. The design of those derivatives involved the modification of the amino-acids in 4- and/or 5-positions of Cyclosporin A.

By modifying amino-acids in 2- and/or 6-positions of Cyclosporin A, Sigal et al. synthesised a total of 61 cyclosporin analogs and observed that such chemical modifications induce a decrease in the immunosuppressive activity (see Sigal et al., J. Exp. Med., 173, 1991, 619-628).

Further attempts for modifying amino-acid in 3-position of Cyclosporin A in order to obtain non-immunosuppressive compounds were described in particular by Barrière et al., in WO 98/28328, WO98/28329, and WO 98/28330.

Wenger et al. have designed a series of compounds that differ from Cyclosporin A in position 3, in which they contain an N-methylated, nonbulky hydrophobic or neutral amino acid other than a glycine, and in position 4, in which they contain an N-methylated or N-ethylated hydrophobic or neutral amino acid other than a leucine and they report that those compounds have a high potency to inhibit HIV-1 replication and essentially lack immunosuppressive activity (see International patent application WO 00/01715 and Tetrahedron Lett., 41, (2000), 7193-6).

Figure 1:
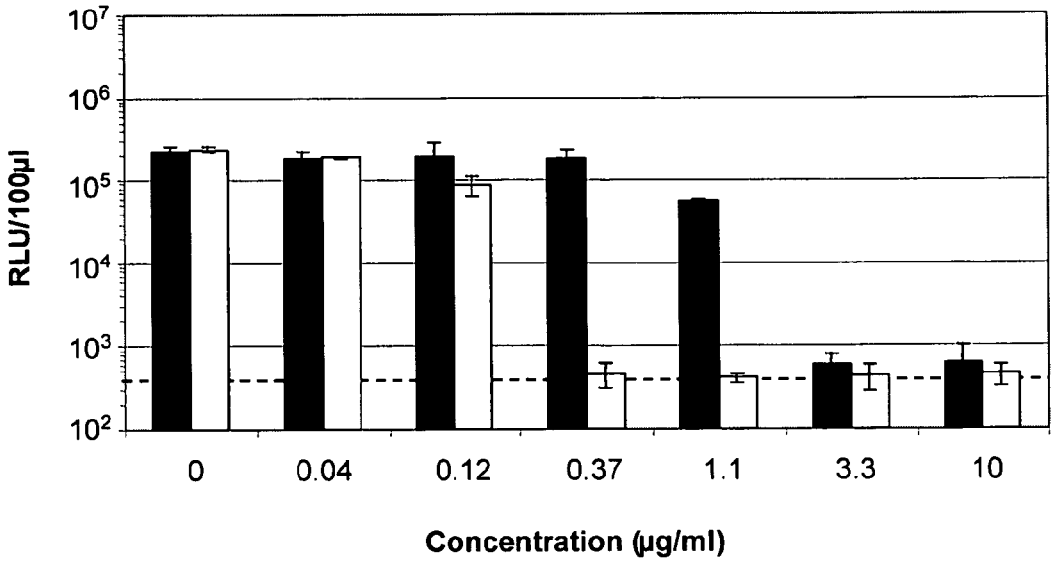
FIG. 1 represents measurements of firefly luciferase activities in relative light units or RLU (ordinate) present in 0.1 ml aliquots of lysates of Huh-7-Lunet cells that were infected with Jc1-Luc recombinant virus and, 4 hours later, exposed to different concentrations (abscissa) of CsA (black or filled bars) or [D-MeAla]$^3$-[EtVal]$^4$-CsA (white or unfilled bars), respectively.

DESCRIPTION OF THE INVENTION:

The aim of the present invention is to provide the clinician with a new therapy for the treatment of HCV infection, particularly e.g. in the case of the prevention of HCV recurrence. This therapy should offer a higher antiviral activity and a better safety profile in comparison to the already approved therapy or the newly proposed ones.

The present inventors surprisingly found that the administration to a patient infected with HCV of a very specific compound, i.e. $[D\text{-}MeAla]^3$-$[EtVal]^4$-CsA, meets the above requirements. They observed that, in addition to its non-immunosuppressive property, $[D\text{-}MeAla]^3$-$[EtVal]^4$-CsA has a significantly increased affinity for cyclophilins, which increased affinity is correlated with an elevated efficacy against inhibition of HCV replication.

Accordingly, one of the subject-matters of the present invention relates to the use of $[D\text{-}MeAla]^3$-$[EtVal]^4$-CsA for the manufacture of a medicinal product intended for the treatment of HCV infection in a patient.

$[D\text{-}MeAla]^3$-$[EtVal]^4$-CsA has been reported by Wenger et al. in WO 00/01715 and it has been attributed the CAS Registry Number 254435-95-5. It is a cyclic undecapeptide described by the following formula:

```
-MeBmt-αAbu-D-MeAla-EtVal-Val-MeLeu-Ala-(D)Ala-
    1    2      3      4   5      6   7     8

MeLeu-MeLeu-MeVal-
   9    10    11
```

where MeBmt is N-methyl-(4R)-4-but-2E-en-1-yl-4-methyl-(L)threonine, αAbu is L-α-aminobutyric acid, D-MeAla is N-methyl-D-alinine, EtVal is N-ethyl-L-valine, Val is L-valine, MeLeu is N-methyl-L-leucine, Ala is L-alanine, (D)Ala is D-alanine, and MeVal is N-methyl-L-valine. The conventional numbering of amino acid positions generally used in reference of Cyclosporin A is shown below the formula. This is achieved by using composite names comprising a first portion indicating the identity of residues that are different from those in cyclosporin A and providing their position, and a second portion labelled "CsA" indicating that all other residues are identical to those in Cyclosporin A. For example, $[Melle]^4$-CsA is a cyclosporin that is identical to cyclosporin A except that MeLeu in position 4 is replaced by Melle (N-methyl-L-isoleucine).

Figure 2:
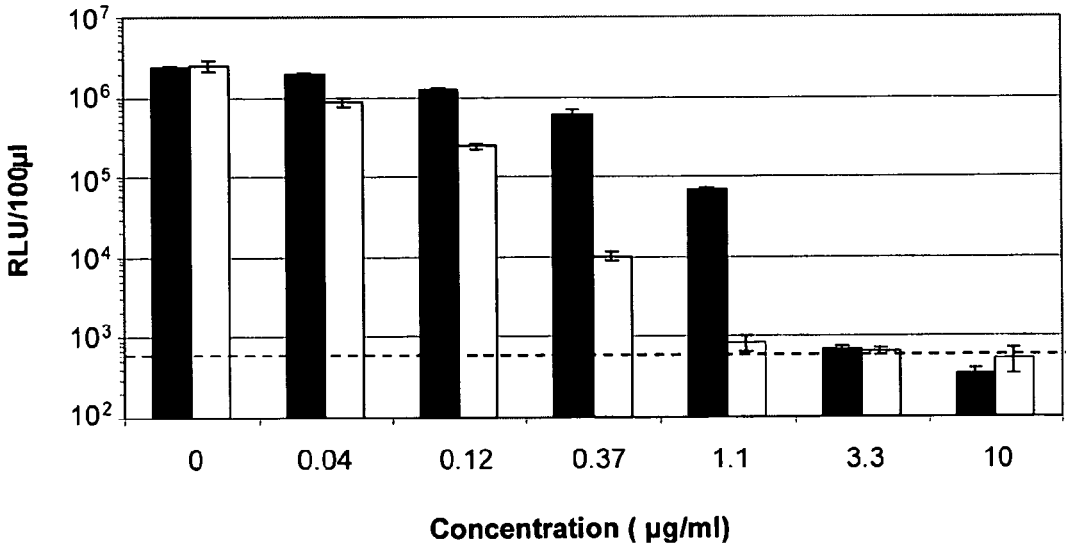
FIG. 2 represents measurements of firefly luciferase activities in relative light units or RLU (ordinate) present in 0.1 ml aliquots of lysates of Huh-7.5 cells that were infected with Jc1-Luc recombinant virus and, 4 hours later, exposed to different concentrations (abscissa) of CsA (black or filled bars) or [D-MeAla]$^3$-[EtVal]$^4$-CsA (white or unfilled bars), respectively.
Figure 3:
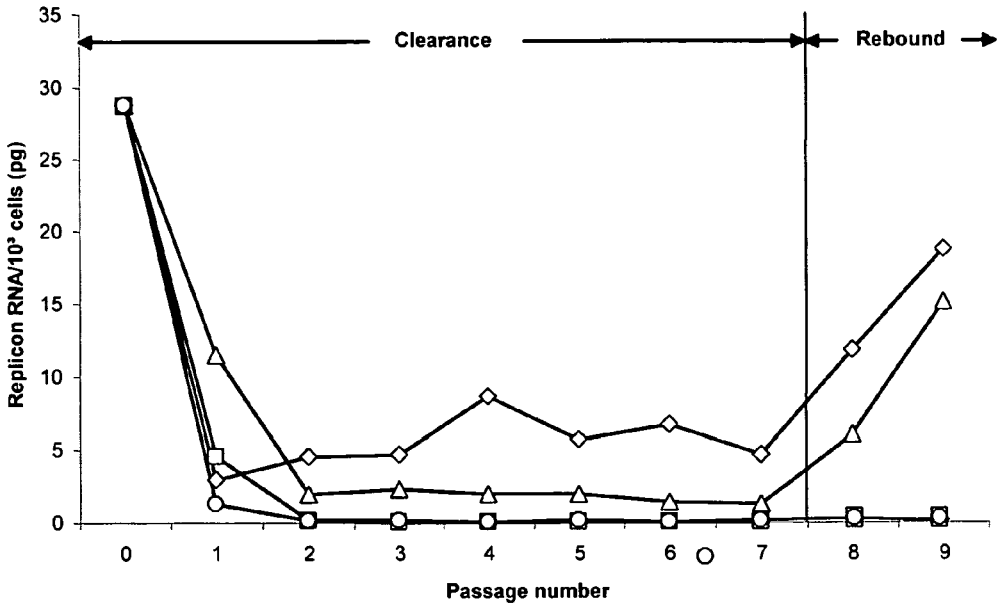
FIG. 3 represents amounts of replicon RNA per 1000 cells (pg) in Huh-9-13 cultures exposed during 7 passages to CsA (diamonds and triangles) or [D-MeAla]$^3$-[EtVal]$^4$-CsA (circles and squares) (clearance phase) and, subsequently, during two additional passages to antibiotic G418 (rebound phase).
Figure 4:
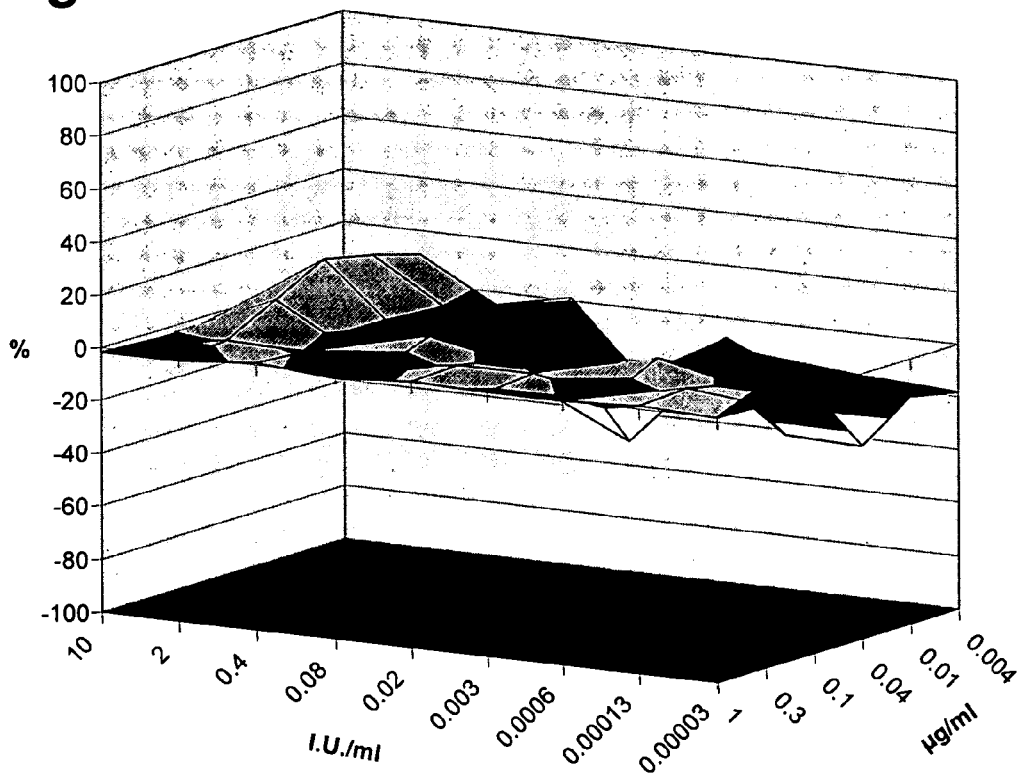
FIG. 4 represents effects of combinations of different concentrations of $[D\text{-}MeAla]^3$-$[EtVal]^4$-CsA and interferon-α 2a on replication of HCV replicons in Huh-5-2 cells. The horizontal axes represent interferon-α 2a concentrations in I.U./ml and $[D\text{-}MeAla]^3$-$[EtVal]^4$-CsA concentrations in μg/ml. The vertical axis reveals deviations from calculated additive effects of the two drugs, a positive deviation indicating a greater efficacy, and a negative deviation indicating a smaller efficacy compared to calculated efficacy.

The present invention will be explained further with following experiments and with the drawing in which:

FIG. 1 represents a dose response histogram measured by luciferase assay in infected Huh-7-Lunet cells;

FIG. 2 represents a dose response histogram measured by luciferase assay in infected Huh-7.5 cells;

FIG. 3 represents clearance response curves of infected Huh-9-13 cells;

FIG. 4 represents 3D representation of dose response with combination IFN/$[D\text{-}MeAla]^3$-$[EtVal]^4$-CsA.

Current medical uses of Cyclosporin A relate to the ability of this compound to suppress the cell-mediated immune response by preventing production and release of several autocrine T-cell growth factors, including interleukin 2 (IL-2), from activated T cells (see Borel (1989) Transplant. Proceed. 21, 810-815; Kronke et al. (1984) Proc. Natl. Acad. Sci. USA 81, 5214-5218; Faulds et al. (1993) Drugs 45, 953-1040). Upon entry into cells, Cyclosporin A binds to cyclophilins with high affinity (see Handschumacher et al. (1984) Science 226, 544-547). As among different biological function, they have peptidyl-prolyl cis-trans isomerase (PPlase) activity that can be measured in vitro (see Fischer et al. (1989) Nature 337, 476-478; Takahashi et al. (1989) Nature 337, 473-475). Critical for the immunosuppressive effect of cyclosporin A is an interaction between cyclophilin-Cyclosporin A complex and calcium- and calmodulin-dependent serine/threonine phosphatase 2B (calcineurin) (see Hauske (1993) DN&P 6, 705-711, Friedman et al. (1991) Cell 66, 799-806; Liu et al. (1991) Cell 66, 807-815). Formation of this ternary complex results in an inhibition of the phosphatase activity of calcineurin. (see Jain et al. (1993) Nature 365, 352-355; Rao et al. (1997) Annu. Rev. Immunol. 15, 707-747; Crabtree (1999) Cell 96, 611-614). Calcineurin promotes the selective dephosphorylation of NF-AT that then translocates to the nucleus where it associates with activator protein 1 and transactivates target genes, including the IL-2 gene.

It is believed that, due to the amino-acids in 3- and 4-positions, $[D\text{-}MeAla]^3$-$[EtVal]^4$-CsA has a dramatically reduced ability to interact with calcineurin as shown by transcriptional and immunological assays as well as a significantly increased affinity for cyclophilins as indicated by assays of inhibition of peptidyl-prolyl cis-trans isomerase activity.

Peptidyl-prolyl cis-trans isomerase (PPlase) activity of cyclophilins was determined using a procedure adapted from Kofron et al. (see Biochemistry 30, 6127-6134 (1991); J. Am. Chem. Soc. 114, 2670-2675 (1992)). N-succinylated Ala-Ala-Pro-Phe-para nitro-aniline (Suc-AAPF-pNA, Bachem, Bubendorf, Switzerland) was used as the substrate. The assay was based on the preferential chymotrypsin cleavage of the trans isoform of the Phe-pNA bond in the tetrapeptide Ala-Ala-Pro-Phe-pNA. This cleavage liberates the para-nitroaniline moiety that can be detected and quantitated at 390 nm ($\epsilon$=11,814 $M^{-1}cm^{-1}$). Schutkowski et al. (1995) Biochemistry 34, 13016-13026. Cis-trans isomerization is catalysed by cyclophilin (PPlase, EC 5.2.1.8). After mixing CsA or another cyclosporin ($10^{-9}$-$2\times10^{-5}$ M final concentrations prepared from 1000-fold concentrated stock solutions in ethanol) with 0.1 μg cyclophilin (Sigma) in a total volume of 1.5 ml of 40 mM Hepes, pH 7.9, and incubation for 50 min on ice, the reaction mixture was transferred to a cuvette that was kept at 10° C. in a Varian spectrophotometer (Varian). Subsequent to the addition of 3.75 mg of chymotrypsin (70 μl of a solution of chymotrypsin in 10 mM HCl), the reaction was initiated by addition of 10 μl of a 3.2 mM solution of Suc-AAPF-pNA in 0.5 M LiCl/trifluoroethanol. The reaction was monitored for 3 min, and an initial rate constant was determined from the data obtained. As a control, an initial rate constant was also determined for a parallel reaction that lacked cyclophilin. Concentration-response curves were established for cyclosporin A and other cyclosporins, and $IC_{50}$ (50% inhibitory concentration) values of different cyclosporins were expressed relative to that of cyclosporin A (1.0). A value less than 1 means that the compound has an higher cyclophilin affinity than CsA.

A NF-AT-dependent reporter assay was used initially to estimate immunosuppressive activities of cyclosporins. Baumann et al. (1992) Transplant. Proc. 24, 43-48. Jurkat T cells stably transfected with a reporter construct containing a bacterial β-galactosidase gene under the control of a promoter of an IL-2 gene were obtained from G. Zenke, Novartis Pharma AG, Basel, Switzerland. The cells were grown in RPMI1640 medium supplemented with 10% heat-inactivated fetal calf serum, 100 u/ml penicillin, 100 μg/ml streptomycin, 2 mM glutamine, 50 μM 2-mercaptoethanol and 100 u/ml hygromycin B. The cells were stimulated by the addition of 2.4 μM phorbol-12-myristate-13-acetate and 75 μg/ml phytohemagglutinin in the presence or absence of cyclosporin A or another cyclosporin ($10^{-9}$-$2\times10^{-5}$ M final concentrations prepared from 1000-fold concentrated stock solutions in ethanol). Subsequent to incubation for 20 h at 37° C., cells were harvested and lysed in 50 mM $Na_2HPO_4$ (pH 9.0), 10 mM KCl, 1 mM $MgSO_4$, 1% Triton X-100, 0.5 mM 4-methylumbelliferyl-β-D-galactoside (Sigma, Buchs, Switzerland). The β-galactosidase reaction was allowed to proceed for 1 h in the dark at room temperature. Fluorescent 4-methyl-umbelliferone was assayed fluorometrically in the supernatant solution (excitation: 355 nm; emission: 460 nm). Concentration-response curves were established for cyclosporin A and other cyclosporins, and the $IC_{50}$ values of different cyclosporins were calculated relative to that of cyclosporin A (1.0). A value higher than 1 means that the compound is less immunosuppressive than CsA.

Example results are shown in Table 1 below.

TABLE 1

Cyclophilin binding (PPIase) and immunosuppressive (IL-2) activities of CsA and other cyclosporins

| Compound | PPIase | IL-2 |
|---|---|---|
| CsA | 1.0 | 1.0 |
| [D-MeAla]$^3$-[EtVal]$^4$-CsA | 0.3 | 7161 |
| [MeIle]$^4$-CsA | 0.5 | 2250 |

The data shown in Table 1 revealed that certain substitutions in position 4 (i.e., Val, Ile) dramatically reduced immunosuppressive activity (measured as inhibition of IL-2 expression) as well as detectably enhanced cyclophilin binding activity (measured as inhibition of PPIase activity of cyclophilin). Substitution in position 3 resulted in a substantial further increase in cyclophilin binding activity (by 2 fold or more; cf [D-MeAla]$^3$-[EtVal]$^4$-CsA. It had a higher cyclophilin binding activity and a lower residual immunosuppressive activity than [MeIle]$^4$-CsA, the best reference compound available from the literature. [MeIle]$^4$-CsA is also known as NIM811.

Non-Immunosuppressive Activity of [D-MeAla]$^3$-[EtVal]$^4$-CsA

In a confirmatory analysis, immunosuppressive activities of CsA, [MeIle]$^4$-CsA and [D-MeAla]$^3$-[EtVal]$^4$-CsA were estimated using the mixed lymphocyte reaction. In this assay, cyclosporins were dissolved in ethanol (10 mg/ml). Freshly isolated CD4$^+$ PBMCs from two healthy donors were mixed subsequent to inactivation by irradiation of one of the populations (stimulator cells; S). After five days of co-culture in the presence or absence of a cyclosporin (1 μg/ml), the proliferative response of the non-inactivated cell population (responder cells; R) was determined by [$^3$H]-thymidine incorporation.

The assay was conducted reciprocally with the two cell populations, each being inactivated and stimulated in turn. Stimulation (%) of responder cells was calculated by the formula:

Percent stimulation=100×(sample with cyclosporin−background)/(sample without cyclosporin−background)

Sample refers to a mixture of stimulator and responder cells. Background represents a control in which only stimulator cells are mixed. Results are shown in Table 2. They were interpreted to mean that both [MeIle]$^4$-CsA and [D-MeAla]$^3$-[EtVal]$^4$-CsA are essentially devoid of immunosuppressive activity.

TABLE 2

Proliferative response of CD4$^+$ PBMCs in the presence/absence of cyclosporins

| Co-culture | Compound | N | % Stimulation (relative) | Standard deviation |
|---|---|---|---|---|
| R1 × S2 | None | 8 | 100 | 30 |
| R1 × S2 | CsA | 4 | 29 | 3 |
| R1 × S2 | [MeIle]$^4$-CsA | 4 | 84 | 13 |
| R1 × S2 | [D-MeAla]$^3$-[EtVal]$^4$-CsA | 4 | 75 | 11 |
| R2 × S1 | None | 8 | 100 | 9 |
| R2 × S1 | CsA | 4 | 9 | 2 |
| R2 × S1 | [MeIle]$^4$-CsA | 4 | 75 | 9 |
| R2 × S1 | [D-MeAla]$^3$-[EtVal]$^4$-CsA | 4 | 65 | 7 |
| S1 × S2 | None | 4 | 0 | 0.6 |

R1 × S2 refers to a co-culture of responder cells from donor 1 and stimulator cells from donor 2.
N is the number of measurements.

High Anti-HCV Activity and Low Cytotoxicity/Cytostatic Effect of [D-MeAla]$^3$-[EtVal]$^4$-CsA As mentioned previously, infection with hepatitis virus C(HCV) is a serious health problem because persistently infected patients are at a high risk for developing chronic liver diseases including cirrhosis and hepatocellular carcinoma. Current available therapy is inadequate for a large fraction of the latter population as well as is associated with significant side effects. Until recently, development of more effective therapies was hindered by the absence of an appropriate in vitro model of HCV replication that allows screening of potentially active compounds prior to evaluation in human clinical trials. This obstacle was overcome by the development of genetically modified HCV minigenomes (replicons) that self-amplify in cultured hepatoma cells to high levels (Lohmann et al. Science 285, (1999), 110-113). This HCV replicon system has rapidly become the standard tool for studying HCV replication, pathogenesis and persistence (Bartenschlager et al. Antiviral Res. 60, (2003), 91-102). The HCV genome consists of a single-stranded RNA that contains a single open reading frame for a polyprotein of about 3000 amino acids. Translation of this polyprotein is initiated at an internal ribosome entry site (IRES) located at the 5' end of the RNA. The HCV polyprotein is cleaved into at least ten proteins. They include capsid protein C, envelope proteins E1 and E2, possible viroporin protein p7, non-structural proteins NS2 and NS3 having serine proteinase as well as ATPase/helicase activities, NS4A, membraneous web-inducing protein NS4B, NS5A and RNA-dependent RNA polymerase NS5B. The first successful replicon was a bicistronic RNA containing in a 5' to 3' direction an HCV IRES, a coding sequence for a neomycin phosphotransferase, an IRES from an encephalocarditis virus and coding sequences for HCV proteins NS3 to NS5. Subsequent to introduction into Huh-7 cells and selection using G418 (geneticin), this replicon could be shown to replicate autonomously to high levels (1,000-5,000 copies/cell) (Lohmann et al., 1999). Characterization of the system revealed that replication efficiency depended on permissiveness of the host cell and, importantly, on the selection of cell culture-adaptive mutations in the HCV protein-coding sequences. Replication was found to be sensitive to interferon alpha, providing evidence for the relevance of the system for screening drugs that have in vivo efficacy. Variant replicons were also constructed in which the neomycin phosphotransferase-coding sequence was replaced, e.g., by a luciferase-coding sequence or by sequences coding for a luciferase-ubiquitin-neomycin phosphotransferase fusion protein. Replication of the latter variant replicons can be assayed by the convenient luciferase assay, whereas replication of the former replicon requires determinations of RNA copy number.

Watashi et al. (2003) demonstrated by Northern blot and quantitative RT-PCR (reverse transcriptase polymerase chain reaction) that HCV RNA accumulation was inhibited by CsA but not by the immunosuppressive macrolide FK506 and the non-immunosuppressive CsA derivative PSC 833 in HCV replicon-containing MH-14 cells. Their assays that involved 7-day exposures of cells to active agents revealed that HCV RNA titer was reduced by about 200 fold in the presence of 1 μg/ml cyclosporin A. They further found that non-immunosuppressive cyclosporin [Melle]$^4$-CsA also inhibited HCV replication. Results indicated that [Melle]$^4$-CsA was about equally as effective as CsA in reducing HCV RNA titer.

To determine whether the cyclosporin of the present invention has anti-HCV activity and, should it has such activity, how this activity compares with the activities of CsA and [Melle]$^4$-CsA, experiments were carried out that compared inhibitory effects of CsA, [Melle]$^4$-CsA and [D-MeAla]$^3$-[EtVal]$^4$-CsA in HCV replicon systems.

Assays used Huh 5-2 cells that contained a bicistronic RNA encoding a firefly luciferase-ubiquitin-neomycin phosphotransferase fusion protein and HCV proteins NS3-5. The viral sequences originated from an HCV virus of genotype 1 b. Cells were cultured in RPMI 1640 medium (Gibco) supplemented with 10% fetal calf serum, 2 mM glutamine (Life Technologies), 1× non-essential amino acids (Life Technologies), 100 u/ml penicillin, 100 μg/ml streptomycin and 250 μg/ml G418 (Geneticin, Life Technologies) at 37° C. and 5% $CO_2$. For antiviral (replication) assays, cells were seeded at a density of 7000 cells/well in 96-well View Plates™ (Packard) in the same medium except for G418. After a 24-h incubation, medium was removed, serial dilutions of test compounds in medium were added, and cells were incubated for an additional 72 h.

Antiviral effects were estimated either by luciferase assay or quantitative RT-PCR. To carry out luciferase assays, medium was removed, and cells were washed with PBS. Subsequent to lysis in 50 μl of Glo-lysis buffer (Promega) for 15 min, 50 μl of Stead-Glo Luciferase Assay Reagent (Promega) were added to cell lysates. Luciferase activity was measured using a luminometer, and the signal from each test well was expressed as a percentage of the signal measured in wells of cultures not exposed to a test compound.

Cell density and cytostatic effects were estimated in parallel cultures in regular 96-well plates (Beckton-Dickinson) using the MTT assay (CellTiter 96$^R$ $AQ_{ueous}$ Non-Radioactive Cell Proliferation Assay, Promega). In this assay, 3-(4,5-dimethylthiazol-2-yl)-5-(3-carboxymethoxy-phenyl)-2-(4-sulfophenyl)-2H-tetrazolium (MTS) is bioreduced to a formazan that is quantitated at 498 nm in a plate reader. Formazan production is directly correlated with number of life cells.

RT-PCR analysis quantitated the neomycin region of replicons using an ABI PRISM 7700 sequence detector (Applied Biosystems, Foster City, Calif.). The forward and reverse primers used were 5'-CCGGCTACCTGCCCATTC-3' and 5'-CCAGATCATCCTGATCGACMG-3', respectively SEQ ID: 1, SEQ ID NO: 2. The fluorogenic probe was 5'-ACATCGCATCGAGCGAGCACGTAC-3'SEQ ID No: 3. As an internal control, a plasmid containing part of the neomycin phosphotransferase gene sequence was used.

Results from these experiments permitted calculation of $EC_{50}$ for the different cyclosporins, which is the effective concentration required to inhibit HCV replicon replication by 50%, and of $CC_{50}$, which is the concentration required that inhibits the proliferation of exponentially growing cells by 50%, and a selectivity index SI, which is the ratio between $CC_{50}$ and $EC_{50}$.

Table 3 shows values obtained from Huh 5-2 cells using luciferase activity assays for estimation of replication efficiency and MTT assays for calibration of luciferase assays and for estimation of cytostatic effects of compounds. In agreement with the above-discussed observations by Watashi et al. (2003), CsA and [Melle]$^4$-CsA had similar anti-HCV (replication) activities.

Surprisingly, [D-MeAla]$^3$-[EtVal]$^4$-CsA was considerably more potent than CsA and [Melle]$^4$-CsA. It was also noted that the 50% cytostatic concentration (CC50) for [D-MeAla]$^3$-[EtVal]$^4$-CsA was significantly higher than the values determined for CsA and [Melle]$^4$-CsA. Consequently, a considerably higher selectivity index was found for [D-MeAla]$^3$-[EtVal]$^4$-CsA as compared to the two other cyclosporins. Analogous experiments in which $EC_{50}$ values were derived from determinations of RNA titers using quantitative RT-PCR yielded similar conclusions. SI values of 45*, 73 and 625* were obtained for CsA, [Melle]$^4$-CsA and [D-MeAla]$^3$-[EtVal]$^4$-CsA, respectively. Asterisks indicate that the lower of two independently determined values are presented.

TABLE 3

$EC_{50}$, $CC_{50}$ and SI values determined from luciferase assays of HCV RNA replication and MTT assays of cytotoxicity in Huh 5-2 cells comprising a luciferase-containing HCV minireplicon

| Compound | $EC_{50}$ (μg/ml) +/− Std. Dev. | $CC_{50}$ (μg/ml) +/− Std. Dev. | Selectivity index |
|---|---|---|---|
| CsA | 0.28 +/− 0.13 | 11.6 +/− 5.6 | 41 |
| [D-MeAla]$^3$-[EtVal]$^4$-CsA | 0.03 +/− 0.04 | >27 | >900 |
| [MeIle]$^4$-CsA | 0.22 | 14 | 64 |

Antiviral Activity of [D-MeAla]$^3$-[EtVal]$^4$-CsA Measured in Infected Target Cells with Recombinant HCV The anti-HCV activity of [D-MeAla]3-[EtVal]4-CsA compared to CsA was further determined in culture systems approaching the in vivo situation. The method used hepatoma cells that had been infected with an infectious full length cheieric HCV construct or the same virus that was modified to carry a luciferase receptor gene. After the treatment of the infected cells with the cyclosporin of the invention or CsA, the luciferase activity was measured as being directly correlated to the inhibition of the viral replication.

Infectious HCV viruses of full-length chimeric genome between HCV strains J6 and JFH1 (Jc1) were used to inoculate the hepatoma cells of the assays. The construct of Jc1 virus was also modified to obtain a bicistronic genome carrying a luciferase reporter gene (Jc1-Luc). Twenty-four and ninety-six hours after the transfection of RNA transcripts of the genomes by electroporation of Huh-7.5 cells, cell culture supernatant was collected. Supernatants were filtered (0.45 μM) and cell culture infectious dose 50 (CCID50) per ml were determined by the limiting dilution assays according to Lindenbach et al. (Science, 309, (2005), 623-626). The CCID50 were 1.3×105 for Jc1 and 4.2×103 for Jc1-Luc.

Assays used either Huh-7-Lunet or Huh-7.5 cells (Lohmann et al., Science 285(5424), (1999), 110-113). Cells were grown in Dulbecco's modified Eagle's Medium (DMEM;

Gibco) supplemented with 10% heat-inactivated fetal bovine serum (FCS) (Integro), 1× non-essential amino acids (Gibco), 100 IU/ml penicillin (Gibco), 100 μg/ml streptomycin (Gibco) or 25 μg/ml hygromycin (Gibco) for Huh-mono cells at 37° C. and 5% CO2. For antiviral (replication) assays, Huh-7-Lunet and Huh-7.5 cells were seeded at a density of 2×104 or 4×104 cells per well of a 12-well plate. Twenty four hours later, the medium was replaced by 0.5 ml of the Jc1-Luc virus stock (12-well plates) or 0.25 ml of the Jc1 virus stock (12-well plates). Four hours later, the virus inoculum was replaced by medium containing different concentrations of CsA or [D-MeAla]3-[EtVal]4-CsA and were further incubated for an additional 72 hours.

The inhibition of viral replication were estimated by luciferase assay. To carry out luciferase assay, cells were harvested, washed with PBS and lysed in luciferase lysis buffer (1% Triton X-100, 25 mM glycylglycine, 15 mM MgSO4, 4 mM EGTA, and 1 mM DTT). Firefly luciferase activity was measured according to Krieger et al. (J Virol, 75(10), (2001), 4614-4624). Briefly, after one freeze/thaw cycle, cells were resuspended and 100 μl of cell lysate was mixed with 360 μl assay buffer (25 mM glycylglycine, 15 mM MgSO4, 1 mM DTT, 2 mM ATP, 15 mM potassium phosphate buffer, pH 7.8) and 200 μl substrate solution (200 mM luciferin, 25 mM glycylglycine). Finally, luminescence was measured by using a Lumat LB9507 luminometer (Berthold) for 20 samples.

In these examples (FIGS. 1 and 2), both $[D\text{-}MeAla]^3$-$[EtVal]^4$-CsA (white bars) and CsA (black bars) resulted in a dose-dependent antiviral activity, whereby $[D\text{-}MeAla]^3$-$[EtVal]^4$-CsA proved again superior over CsA, thus corroborating the data obtained with the subgenomic replicons. A 10-fold higher concentration of CsA was needed to result in the same replication inhibiting effect as the cyclosporin of the invention.

High Affinity of the Cyclosporin of the Invention for Cyclophilin

In the above-discussed observations by Watashi et al. (2003) and Nagakawa et al. (2003), the anti-HCV effect was related to the binding capacity of cyclosporins to the cyclophilins The effects on the PPIase activity of CsA, $[Melle]^4$-CsA and $[D\text{-}MeAla]^3$-$[EtVal]^4$-CsA was measured for cyclophilins to determine the more potent inhibitor of PPIase activity of cyclophilin, e.g. cyclophilin A, and, consequently, of HCV replication.

Commercial human recombinant cyclophilin A (Sigma) was used in the assays. PPIase activity of cyclophilins was determined using a chymotrypsin-coupled spectrophotometric assay according to Garcia-Echverria et al. (BBRC, 191, (1993), 70-75). This method is based on the high trans selectivity of chymotrypsin for peptides of the type N-succinyl-ala-ala-pro-phe-p-nitroanilide. The peptides cleavage liberated the para-nitroaniline moiety that could be detected and quantitated at 390 nm. The hydrolysis of the cis form was limited by the rate of cis-trans isomerisation carried out by cyclophilin A. The peptide was made up in a solution of 25 nM LiCl in 2,2,2-trifluoroethanol at 470 mM to enhance the cis conformer peptides population. The assay was performed on the split beam spectrophotometer and the water bath was set at 5° C. Cyclophilin A (7500 pmol/mg total enzyme concentration; Sigma) were dissolved at 20 nM in a buffer (35 mM HEPES and 0.26 mg/ml chymotrypsin (specific activity 50 units/mg), pH 7.8 with KOH) and were incubated for 6 minutes at room temperature followed by 54 minutes in the water bath. CsA, $[Melle]^4$-CsA or $[D\text{-}MeAla]^3$-$[EtVal]^4$-CsA were added as appropriate in these incubations using a concentration range of 2-50 nM. Then 3.5 ml of the incubated cyclophilin was added to the sample cuvette. The reference cuvette contained a reaction that had gone to completion to balance the reference beam. Peptide was added at 25 μM to initiate the reaction and the change in absorbance was monitored at 10 data points per second. As a control, rates were also determined for a parallel reaction that lacked cyclophilin. These blank rates of peptide hydrolysis (i.e. in the absence of cyclophilin) were subtracted from rates in the presence of cyclophilin A.

The initial rates obtained from the PPIase assays were analysed by first order regression analysis by using first order transformation of the traces of the time course of the change in the absorbance at 390 nm. Total enzyme concentration ($E_t$), the inhibitor dissociation constant ($K_i$) and the rate constant for the rate limiting reaction was calculated with the software FigSyS (2003, Biosoft) by fitting the data obtained from the regression analysis in the tight binding inhibitor multiprotein equation.

The tight binding inhibitor multiprotein equation had the following formula:

$$v=k*E_t*P-k*(-b-\mathrm{sqrt}(b*b-4*c))/2$$

where b is defined as $b=-(E_t*P+I+K_i)$ and c is $c=Et*P*I$.

Once Et, $K_i$ and k were calculated by the computer for a given set of data, a graphic representation of the data was plotted and the line fitted to the points assuming tight inhibitor binding to a single protein, defined by the following equations:

$$v=K*E_t*P-K(B-\mathrm{sqrt}(B*B-4*C))/2$$

where $B=E_t*P+I+K_i$ and $C=E_t*P*I$.

TABLE 4

$E_t$, $K_i$ and k values of cyclophilin A for CsA, $[MeIle]^4$-CsA and $[D\text{-}MeAla]^3$-$[EtVal]^4$-CsA determined from PPIase activity assays.

| Compound | $E_t$ (pmol/mg) | $K_i$ (nM) | k (s − 1) |
|---|---|---|---|
| CsA | 7500 | 9.79 ± 1.37 | 0.17 ± 0.0069 |
| $[MeIle]^4$-CsA | 7500 | 2.11 ± 0.32 | 0.17 ± 0.0068 |
| $[D\text{-}MeAla]^3$-$[EtVal]^4$-CsA | 7500 | 0.34 ± 0.12 | 0.16 ± 0.0074 |

The lowest $K_i$ of cyclophilin A observed for the cyclosporin of the invention corroborated the high potent of antiviral activity, the specificity and selectivity index (as above-mentioned) compared to CsA and $[Melle]^4$-CsA. Surprisingly, the non-immunosuppressive $[D\text{-}MeAla]^3$-$[EtVal]^4$-CsA showed an almost 6-fold higher affinity for the cyclophilin of the example compared to the other non-immunosuppressive cyclosporin $[Melle]^4$-CsA.

The above-described experimentation provided that $[D\text{-}MeAla]^3$-$[EtVal]^4$-CsA was a more effective inhibitor of HCV replication than any other tested cyclosporin. This increased anti-HCV activity correlated with the increased cyclophilin binding activity of $[D\text{-}MeAla]^3$-$[EtVal]^4$-CsA.

HCV Replicon Clearance and Rebound

The recurrence of HCV infection is a major problem of the disease especially even with the use of potential efficient treatment, e.g. cyclosporin and/or Interferon. To study whether the more potent anti-HCV activity of the cyclosporin of the invention as compared to CsA is reflected in the ability of the compound to more efficiently cure cells producing HCV replicon from those, an in vitro cell assay was performed based on presence of the selective drug G418 for recombinant produced replicon.

Assays used Huh-9-13 cells, human hepatoma cells (Huh-7) (Lohmann et al., Science 285(5424), (1999), 110-113) Cells were grown in the usual complete medium DMEM without G418 pressure. The cells were cultured in the presence of either CsA or $[D\text{-}MeAla]^3$-$[EtVal]^4$-CsA (both at 0.5 or 1 μg/ml) or were left untreated for 7 consecutive passages. Control was performed to guarantee that the absence of the G418 selective pressure would not influence the HCV replicon content during several passages. To confirm that Huh-9-13 cells that had been treated for 7 days with [D-MeAla]$^3$-[EtVal]$^4$-CsA were indeed cleared from their replicon, G418 selection (1000 μg/ml) was restarted for 2 more passages. Only those cells that were still carrying the HCV replicon have been able to proliferate under these conditions and cells without replicon have died in the presence of G418 during the rebound phase.

RT-PCR were performed on extracts of viral RNA of samples taken at different passage points. The forward and reverse primers used were 5'-CCGGCTACCTGCCCATTC-3' and 5'-CCAGATCATCCTGATCGACMG-3', respectively. The fluorogenic probe was 5'-ACATCGCATCGAGCGAG-CACGTAC-3'. As an internal control, a plasmid containing part of the neomycin phosphotransferase gene sequence was used. Results were analysed and expressed as a quantity of replicon RNA (ng) per 1'000 cells and used to draft a graph.

Results from these experiments (FIG. 3) showed the superior antiviral effect of [D-MeAla]$^3$-[EtVal]$^4$-CsA compared to CsA in this standard in vitro cell assay. Surprisingly, the cyclosporin of the invention showed virucidal effect and not only virustatic effect as the other immunosuppressive CsA. Indeed, when the [D-MeAla]$^3$-[EtVal]$^4$-CsA treated Huh-9-13 cells (circles and square in FIG. 3) were again cultured in the presence of G418 (rebound phase), the cultures died compared to CsA treated cells (diamond and triangle). Both cultures that had been treated with CsA for 7 consecutive passages were able to proliferate in the presence of G418. This confirmed that [D-MeAla]3-[EtVal]4-CsA was able to cure Huh-9-13 cells from their HCV replicon.

Drug Combination

Interferon (IFN) is part of the current therapy of HCV infection. The effect of [D-MeAla]3-[EtVal]4-CsA/IFN-α 2a combination was evaluated using the method of Prichard and Shipman (Antiviral Res, 1990, 14, 181-205). In brief, the theoretical additive effect is calculated from the dose-response curves of individual compounds by the equation of formula:

$$Z=X+Y(1-X),$$

where X represents the inhibition produced by [D-MeAla]3-[EtVal]4-CsA alone and Y represents IFN-α 2a alone. Z represents the effect produced by the combination of [D-MeAla]3-[EtVal]4-CsA with IFN-α 2a. The theoretical additive surface is subtracted from the actual experimental surface, resulting in a horizontal surface that equals the zero plane when the combination is additive, a surface that lies above the zero plane indicates a synergistic effect of the combination and a surface below the zero plane indicates antagonism. The antiviral assay was carried out essentially as described above for Huh 5-2 cells except that compounds were added in checkerboard format. For each compound three replicate plates were used to measure the dose response curve of each individual compound. The data obtained from all three plates were used to calculate the theoretical additive surface. Combination studies for each pair of compounds were also done in triplicate. Data were analysed for variance by the ANOVA test.

A slight synergistic activity was noted at the highest concentrations of IFN-α 2a used, but overall the combined anti-HCV activity of [D-MeAla]3-[EtVal]4-CsA with IFN-α 2a can be considered as additive (FIG. 4).

The findings with [D-MeAla]$^3$-[EtVal]$^4$-CsA can be summarized as follows:

- [D-MeAla]3-[EtVal]4-CsA has a more potent anti-HCV activity and is less cytotoxic than CsA, as shown in an HCV subgenomic replicon system.
- This has been confirmed in an hepatoma cell culture infected with a full-length infectious chimeric genome between HCV strains J6 and JFH1.
- [D-MeAla]3-[EtVal]4-CsA is able to cure cells from their HCV replicon more efficiently than CsA
- These effects are related to a more pronounced cyclophilin binding affinity.

The anti-HCV activity of the combination [D-MeAla]3-[EtVal]4-CsA/IFN-α 2a is additive.

[D-MeAla]$^3$-[EtVal]$^4$-CsA can be used to treat patients infected with HCV. The active compound may be administered by any conventional route. It may be administered parentally, e.g., in the form of injectable solutions or suspensions, or in the form of injectable deposit formulations. Preferably, it will be administered orally in the form of solutions or suspensions for drinking, tablets or capsules. Pharmaceutical compositions for oral administration comprising a cyclosporin of the invention are described in Examples. As is demonstrated by the examples, such pharmaceutical compositions typically comprise a cyclosporin of the invention and one or more pharmaceutically acceptable carrier substances. Typically, these compositions are concentrated and need to be combined with an appropriate diluent, e.g., water, prior to administration. Pharmaceutical compositions for parenteral administration typically also include one or more excipients. Optional excipients include an isotonic agent, a buffer or other pH-controlling agent, and a preservative. These excipients may be added for maintenance of the composition and for the attainment of preferred ranges of pH (about 6.5-7.5) and osmolarity (about 300 mosm/L).

Additional examples of cyclosporin formulations for oral administration can be found in U.S. Pat. Nos. 5,525,590 and 5,639,724, and U.S. Pat. Appl. 2003/0104992. By the oral route, the indicated dosage of a cyclosporin of the invention for daily to trice weekly administration may be from about 1 mg/kg to about 100 mg/kg, preferably from about 1 mg/kg to about 20 mg/kg. By the intravenous route, the indicated corresponding dosage may be from about 1 mg/kg to about 50 mg/kg, preferably from about 1 mg/kg to about 25 mg/kg. An effective amount of a cyclosporin of the invention is understood to be an amount that when administered repeatedly in the course of a therapeutic regimen to a patient in need of treatment of HCV infection results in an objective clinical response such as a statistically significant reduction in serum HCV titer or a significant reduction of serum ALT activity in the patient.

Initial phase I clinical studies were carried out to assess the safety of oral doses of [D-MeAla]$^3$-[EtVal]$^4$-CsA, and to determine the pharmacokinetic profile and safety profile of the drug substance. Studies showed that doses of 50 to 1600 mg in a micro-emulsion in water were well tolerated. Mild and short-lived side effects were observed including nausea, vomiting, abdominal pain, mild headaches. These side effects were not dose-related.

Numerous factors will be taken into consideration by a clinician when determining trial doses for testing efficacy of a pharmaceutical composition comprising a cyclosporin of the present invention against HCV infection. Primary among these are the toxicity and half-life of the chosen cyclosporin of the invention. Additional factors include the size of the patient, the age of the patient, the general condition of the patient (including significant systemic or major illnesses including decompensated liver disease, severe preexisting bone marrow compromise and other viral infections), the stage of HCV infection (acute vs. chronic) as indicated, e.g., by serum alanine aminotransferase (ALT) levels, the particular genotype of HCV, previous therapy of HCV infection, the presence of other drugs in the patient, and the like. A course of treatment will require repeated administration of a pharmaceutical composition of the invention. Typically, an adequate drug dose will be administered 3-7 times per week, and duration of treatment may be from about 4 weeks to 6 months, preferably from about 4 weeks to about 12 months. Treatment may be followed by determinations of HCV in serum and measurement of serum ALT levels. The endpoint of treatment is a virological response, i.e., the absence of HCV at the end of a treatment course, several months after initiation of treatment, or several months after completion of treatment. HCV in serum may be measured at the RNA level by methods such as quantitative RT-PCR or northern blots or at the protein level by enzyme immunoassay or enhanced chemiluminescence immuoassay of viral proteins. The endpoint may also include a determination of a serum ALT level in the normal range.

A pharmaceutical composition of the present invention may comprise one or more other ingredients active against HCV infection in addition to a cyclosporin of the present invention such as, for example, another antiviral drug substance, e.g., ribavirin, or an interferon alpha. A cyclosporin of the invention and such other active ingredient can be administered together as part of the same pharmaceutical composition or can be administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and other factors discussed in the previous section. Such additional active ingredients will generally be administered in amounts less than or equal to those for which they are effective as single therapeutic agents. The FDA approved dosages for such active agents that have received FDA approval for administration to humans are publicly available.

All patents, patent applications and publications cited herein shall be considered to have been incorporated by reference in their entirety.

The invention is further elaborated by the following examples. The examples are provided for purposes of illustration to a person skilled in the art, and are not intended to be limiting the scope of the invention as described in the claims. Thus, the invention should not be construed as being limited to the examples provided, but should be construed to encompass any and all variations that become evident as a result of the teaching provided herein.

EXAMPLES

Example 1

Synthesis of [D-MeAla]$^3$-[EtVal]$^4$-CsA (Translated from a Ph.D. thesis by Jean Francois Guichou entitled "De nouveaux analogues de Cyclosporin A comme agent anti-VIH-1", Faculte des Sciences, University of Lausanne, CH-1015 Lausanne, Switzerland (2001)).

Synthesis of H-MeLeu-Val-MeLeu-Ala-D-Ala-MeLeu-MeLeu-MeVal-MeBmt(Oac)-Abu-Sar-OMe:

4-Dimethylaminopyridine (DMAP) (41.5 mmoles; 5.8 g) was added to a solution of cyclosporin A (CsA) (8.3 mmoles; 10 g) in 100 ml acetic anhydride. The solution was stirred for 18 h at room temperature. The reaction mixture was then diluted with 600 ml ethyl acetate, and washed twice with water and four times with a saturated aqueous solution of sodium bicarbonate. The organic phase was dried over anhydrous $Na_2SO_4$, filtered and solvent was evaporated under reduced pressure. The yellow residue obtained was chromatographed on silica gel (eluent: 98:2 dichloromethane/methanol) and recrystallized in ether. 9.5 g of MeBmt(OAc)-CsA, a white powder, were recovered, representing a yield of 92%.

Trimethyloxonium tetrafluoroborate (22.5 mmoles; 3.3 g) was added to a solution of MeBmt(OAc)-Cs (7.5 mmoles; 9.4 g) in 60 ml dichloromethane. After 16 h at room temperature, 35 ml of 0.26 M sodium methanolate in methanol were added. After 1 h, 35 ml of methanol and 35 ml of 2 N sulphuric acid were added, and the reaction mixture was stirred for another 15 min, neutralized to pH 6.0 with saturated $KHCO_3$ (28 ml) and extracted twice with ethyl acetate. The organic phase was washed 2 times with saturated NaCl, dried over anhydrous $Na_2SO_4$ and filtered. Subsequently, solvent was evaporated under reduced pressure. The residue was chromatographed on silica gel (eluent: 5:1 ethylacetate/methanol). 7.3 g of H-MeLeu-Val-MeLeu-Ala-D-Ala-MeLeu-MeLeu-MeVal-MeBmt(OAc)-Abu-Sar-OMe were obtained (yield: 76%).

HPLC tr=268.23 nm (98%)

ES/MS: m/z: 1277.5 [M+H$^+$], 639.2 [M+2H$^+$]

Synthesis of H-Val-MeLeu-Ala-D-Ala-MeLeu-MeLeu-MeVal-MeBmt(OAc)-Abu-Sar-OMe:

DMAP (2.3 mmoles; 334 mg) and phenylisothiocyanate (6.9 mmoles; 0.75 ml) were added to a solution of H-MeLeu-Val-MeLeu-Ala-D-Ala-MeLeu-MeLeu-MeVal-MeBmt (OAc)-Abu-Sar-OMe (4.6 mmoles; 7 g) in 48 ml tetrahydrofuran. After 2 h, solvant was evaporated, and the crude product was chromatographed on silica gel (eluants: 9:1 tert-butyl methyl ether (MTBE)/ethylacetate (1); 9:1 MTBE/methanol (2)). 5.8 g of Ph-NH—C(S)-MeLeu-Val-MeLeu-Ala-D-Ala-MeLeu-MeLeu-MeVal-MeBmt (OAc)-Abu-Sar-OMe were obtained (90% yield).

13.8 ml trifluroracetic acid were added to a solution of the latter compound (4 mmoles; 5.6 g) in 290 ml dichloromethane. After 1 h of reaction, the mixture was neutralized using $KHCO_3$ and diluted with 500 ml dichloromethane. The organic phase was washed 2 times with saturated NaCl, dried over anhydrous $Na_2SO_4$ and filtered. Subsequently, solvent was evaporated under reduced pressure. The residue was chromatographed on silica gel (eluants: 9:1 MTBE/ethylacetate (1); 3:1 MTBE/methanol (2)). 2.8 g H-Val-MeLeu-Ala-D-Ala-MeLeu-MeLeu-MeVal-MeBmt(OAc)-Abu-Sar-OMe were obtained (61% yield).

HPLC tr=25.80 nm (99%)

ES/MS: m/z: 1050.5 [M+H$^+$], 547.7 [M+2H$^+$]

Synthesis of Boc-D-MeAla-EtVal-Val-MeLeu-Ala-D-Ala-MeLeu-MeLeu-MeVal-MeBmt(OAc)-Abu-NMe-$CH_2$—$CH_2$—OH:

Fluoro-N,N,N',-tetramethylformamidinium hexafluorophosphate (TFFH) (0.96 mmoles; 0.25 g) was added, under an inert atmosphere, to a solution of H-Val-MeLeu-Ala-D-Ala-MeLeu-MeLeu-MeVal-MeBmt(OAc)-Abu-Sar-OMe (0.87 mmoles; 1.00 g), DIPEA (2.78 mmoles; 0.48 ml) and Boc-D-MeAla-EtVal-OH (0.96 mmoles; 0.32 g) in 15 ml dichloromethane. After 15 min, dichloromethane was evaporated, and the residue was taken up in ethylacetate. The organic phase was washed successively with a saturated NaHCO solution, a 10% solution of citric acid and a saturated NaCl solution, and was then dried over anhydrous $Na_2SO_4$ and concentrated. Chromatography on silica gel (in 98:2 ethylacetate/methanol) yielded 1.14 g (90%) Boc-D-MeAla-EtVal-Val-MeLeu-Ala-D-Ala-MeLeu-MeLeu-MeVal-MeBmt(OAc)-Abu-Sar-OMe.

The latter product (0.64 mmoles; 0.93 g) was taken up in 45 ml anhydrous methanol, and sodium borohydride (25.5 mmoles; 0.96 g) was added in small portions at 15-min intervals over a period of 3 h 30 min. At 4 h, the reaction mixture was cooled to 0° C., hydrolysed by addition of 10% citric acid and concentrated. Residue was taken up in ethylacetate. The organic phase was washed with a 10% solution of citric acid and a saturated NaCl solution, and was then dried over anhydrous $Na_2SO_4$ and concentrated. After chromatography on silica gel (in 95:5 ethylacetate/methanol) 0.63 g (81%) of Boc-D-MeAla-EtVal-Val-MeLeu-Ala-D-Ala-MeLeu-MeLeu-MeVal-MeBmt(OAc)-Abu-NMe-$CH_2$—$CH_2$—OH were obtained.

ES/MS: m/z: 1434.9 [M+H$^+$], 717.9 [M+2H$^+$]

Synthesis of H-D-MeAla-EtVal-Val-MeLeu-Ala-D-Ala-MeLeu-MeLeu-MeVal-MeBmt-Abu-OH:

Methanesulfonic acid (3.18 mmoles; 2.060 ml) was added to a solution of Boc-D-MeAla-EtVal-Val-MeLeu-Ala-D-Ala-MeLeu-MeLeu-MeVal-MeBmt(OAc)-Abu-NMe-$CH_2$—$CH_2$—OH (0.425 mmoles; 610 mg) in 42.5 ml methanol, and the mixture was heated to and maintained at 50° C. Progress of the reaction was monitored by HPLC and mass spectrometry. After 80 h, the mixture was cooled to 0° C., and hydrolysed by addition of 1 M $NaHCO_3$. Methanol was eliminated, and the residue was taken up in ethylacetate. The organic phase was washed with 1 M $NaHCO_3$ and then a saturated NaCl solution, dried over anhydrous $Na_2SO_4$ and concentrated. The product (557 mg), H-D-MeAla-EtVal-Val-MeLeu-Ala-D-Ala-MeLeu-MeLeu-MeVal-MeBmt(OAc)-Abu-O—$CH_2$—$CH_2$—NHMe, was used in the next step without purification.

Product (0.42 mmoles; 557 mg) was dissolved in 20 ml methanol and combined, under an inert atmosphere, with a solution of sodium methanolate (1.26 mmoles) in 1.26 ml methanol. After 18 h at room temperature, the reaction mixture was cooled to 0° C., and sodium hydroxide (4.2 mmoles; 168 mg) in 5 ml water was added dropwise. After 21 h at room temperature, the reaction mixture was again cooled to 0° C. and neutralized with 1 M $KHSO_4$. Methanol was eliminated, and the residue was dissolved in ethylacetate. The organic phase was washed with a semi-saturated NaCl solution, dried over anhydrous $Na_2SO_4$ and concentrated. The product (335 mg; 64%), H-D-MeAla-EtVal-Val-MeLeu-Ala-D-Ala-MeLeu-MeLeu-MeVal-MeBmt-Abu-OH, was used in the next step without purification.

HPLC tr=26.27 nm (86%)

ES/MS: m/z: 1235.5 [M+H$^+$], 618.2 [M+2H$^+$]

Synthesis of [D-MeAla]$^3$-[EtVal]$^4$-CsA:

Under an inert atmosphere, a solution of H-D-MeAla-EtVal-Val-MeLeu-Ala-D-Ala-MeLeu-MeLeu-MeVal-MeBmt-Abu-OH (0.162 mmoles; 200 mg) and sym.collidine (1.78 mmoles; 0.24 ml) in 50 ml dichloromethane was added dropwise to a solution of (7-azabenzotriazole-1-yloxy)tripyrrolidinophosphonium hexafluoro-phosphate (PyAOP, 0.486 mmoles; 254 mg) in 3.2 liter dichloromethane. 72 h later, the reaction mixture was hydrolysed by addition of a 10% $Na_2CO_3$ solution. Dichloromethane was evaporated, and residue taken up in ethylacetate. The organic phase was washed successively with a 0.1 N HCl solution and a saturated solution of NaCl, dried over anhydrous $Na_2SO_4$ and concentrated. Crude product was purified on silica gel, yielding 110 mg (59%) [D-MeAla]$^3$-[EtVal]$^4$-CsA HPLC tr=30.54 nm (100%)

ES/MS: m/z: 1217.6 [M+H$^+$], 609.3 [M+2H+]

Example 2

Oral Formulations of Cyclosporins of the Invention

Amounts are expressed as % w/w.

Example A

| | |
|---|---|
| Cyclosporin of the invention | 10 |
| Glycofurol 75 | 35.95 |
| Miglycol 812 | 18 |
| Cremophor RH40 | 35.95 |
| Alpha-Tocopherol | 0.1 |

Example B

| | |
|---|---|
| Cyclosporin of the invention | 10 |
| Tetraglycol | 2 |
| Captex 800 | 2 |
| Nikkol HCO-40 | 85.9 |
| Butylhydroxytoluene (BHT) | 0.1 |

Example C

| | |
|---|---|
| Cyclosporin of the invention | 10 |
| Glycofurol 75 | 39.95 |
| Miglycol 812 | 14 |
| Cremophor RH40 | 36 |
| Butylhydroxyanisole (BHA) | 0.05-0.1 |

Example D

| | |
|---|---|
| Cyclosporin of the invention | 10 |
| Tetraglycol | 10 |
| Myritol | 5 |
| Cremophor RH40 | 74.9 |
| Alpha-Tocopherol | 0.1 |

Example E

| | |
|---|---|
| Cyclosporin of the invention | 10 |
| Ethanol | 9 |
| Propylene glycol | 8 |
| Cremophor RH40 | 41 |
| Glycerol monolinoleate | 32 |

For individual components of formulations A-D and for methods of preparation see British Patent Appl. No. 2,222,770.

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<221> NAME/KEY: source
<222> LOCATION:
<223> OTHER INFORMATION: /note="Artificial Sequence Description: primer"

<400> SEQUENCE: 1

ccggctacct gcccattc                                                  18


<210> SEQ ID NO 2
<211> LENGTH: 22
<212> TYPE: DNA
<213> ORGANISM: Artificial Sequence
<220> FEATURE:
<221> NAME/KEY: source
<222> LOCATION:
<223> OTHER INFORMATION: /note="Artificial Sequence Description: primer"

<400> SEQUENCE: 2

ccagatcatc ctgatcgaca ag                                             22


<210> SEQ ID NO 3
<211> LENGTH: 24
<212> TYPE: DNA
<213> ORGANISM: Artificial Sequence
<220> FEATURE:
<221> NAME/KEY: source
<222> LOCATION:
<223> OTHER INFORMATION: /note="Artificial Sequence Description: probe"

<400> SEQUENCE: 3

acatcgcatc gagcgagcac gtac                                           24
```

The invention claimed is:

1. A method of treating hepatitis C infection in a subject comprising administering to the subject an effective amount of [D-MeAla]3-[EtVal]4-CsA.

* * * * *